United States Patent [19]
Schwarze et al.

[11] Patent Number: 6,036,661
[45] Date of Patent: Mar. 14, 2000

[54] APPARATUS FOR ADMINISTERING ACOUSTIC SHOCK WAVES

[75] Inventors: Werner Schwarze, Kreuzlingen; Walter Uebelacker, Buergein, both of Switzerland; Reiner Schulthesis, Salem, Germany; Ruediger Bolze, Reichenau, Germany; Norbert Brill, Constance, Germany

[73] Assignee: HMT Holding AG, Switzerland

[21] Appl. No.: 09/071,016

[22] Filed: May 1, 1998

[30] Foreign Application Priority Data

May 2, 1997 [DE] Germany ............................ 197 18 511

[51] Int. Cl.⁷ .................................................. A61H 01/00
[52] U.S. Cl. ................................................ 601/4; 600/439
[58] Field of Search ..................... 601/4, 15, 17, 601/18, 2, 3; 606/130; 600/411, 437, 439; 378/34, 16, 148, 195, 205, 206, 208, 209

[56] References Cited

U.S. PATENT DOCUMENTS

| | | | |
|---|---|---|---|
| 4,763,652 | 8/1988 | Brisson et al. | 601/4 |
| 4,821,245 | 4/1989 | Riedlinger | 601/15 |
| 4,836,191 | 6/1989 | Noske et al. | 601/4 |
| 4,976,255 | 12/1990 | Reichenberger et al. | 601/4 |
| 5,058,590 | 10/1991 | Wurster | 601/4 |
| 5,123,404 | 6/1992 | Takayama | 601/4 |
| 5,152,289 | 10/1992 | Viebach et al. | 601/4 |
| 5,178,135 | 1/1993 | Uchiyama et al. | 601/4 |
| 5,247,924 | 9/1993 | Suzuki et al. | 601/4 |
| 5,273,027 | 12/1993 | Sekino et al. | 601/4 |
| 5,285,772 | 2/1994 | Rattner | 601/4 |
| 5,301,659 | 4/1994 | Brisson et al. | 601/4 |
| 5,315,986 | 5/1994 | Lacruche et al. | 601/4 |
| 5,327,890 | 7/1994 | Matura et al. | 601/4 |
| 5,590,653 | 1/1997 | Aida et al. | 601/4 |
| 5,618,095 | 4/1997 | Kashima et al. | 362/31 |
| 5,658,239 | 8/1997 | Delmenico | 601/4 |

FOREIGN PATENT DOCUMENTS

| | | |
|---|---|---|
| 3501 838 A1 | 1/1985 | Germany. |
| 3543096 C2 | 12/1985 | Germany. |
| 41 43 540 C2 | 10/1991 | Germany. |
| 195 09 004 C1 | 3/1995 | Germany. |

Primary Examiner—Richard J. Apley
Assistant Examiner—Justine R. Yu
Attorney, Agent, or Firm—Eugene E. Renz, Jr. PC

[57] ABSTRACT

An apparatus for administering ultrasonic shockwaves for medical use includes treatment head for focussing acoustic shockwaves at concretions in human bodies. Clinical treatment often requires two or more treatment heads or several different types of treatment heads with different power requirements to produce fragmentation of concretions. Connectors attached to treatment head cables are provided with electronics containing codes for identifying the type and characteristics of each treatment head and for transmitting that date to a power supply unit. A microprocessor in the power supply unit uses the data provided by the treatment head to automatically deliver the appropriate power ensuring that the treatment head will deliver the correct ultrasonic dose.

In another embodiment, electronics are embedded in the treatment heads to provide the same function as described above.

23 Claims, 3 Drawing Sheets

APPARATUS FOR ADMINISTERING ACOUSTIC SHOCK WAVES

BACKGROUND OF THE INVENTION

Acoustic shock waves are used in human and veterinary medicine for various purposes. Examples are the destruction of concretions (lithotripsy); the induction of bone growth; the treatment of painful orthopedic diseases (insertion treatment, pseudarthrosis); and the treatment of nerves, muscles, and other soft-tissue structures.

Apparatus of the general type in question for administering acoustic shock waves are known from, for example, DE 4,143,540 A1, DE 4,306,460 A1, and DE 4,404,140 A1. In these known apparatus, the pressure pulse source and the focussing device are installed permanently in the apparatus, so that the properties of the generated shock waves and their focussing are inalterably predetermined. The penetration depth of the shock waves, that is, the position of the focus of the shock waves in the area of the body to be treated, is adjusted by means of water-filled cushions, filled to varying degrees with water, which conduct the shock waves into the body.

The preferred source of the pressure waves is an electrical spark gap. Pressure pulse sources based on electro-hydraulic, electromagnetic, and piezoelectric principles are also known. Acoustic lenses or reflectors are used as focussing devices. It is also known that a membrane serving to generate the shock waves or an array of piezoelectric crystals can be designed as a surface of revolution for focussing the waves.

Common to the known apparatus is that they cannot be adapted to different applications or that such adaptation can be achieved only by means of complicated modifications.

SUMMARY OF THE INVENTION

With the foregoing in mind, it is an object of the present invention to improve the design of an apparatus of the general type described above in such a way that a high degree of adaptability to different applications is provided at the same time that the apparatus remains easy to operate.

The basic idea of the invention consists in combining the pressure pulse source, the fluid medium, and the focussing device in a closed treatment head. The treatment head is connected by way of a detachable connection to the power supply unit. It is therefore possible to attach different treatment heads to the complicated supply unit, and, because of the detachable coupling, it is easy to exchange one treatment head for a different treatment head with a different set of characteristics or to replace an old treatment head with a new one. Within the scope of the invention, it is also possible to use two or possibly even more treatment heads with the same or different characteristics simultaneously. As a result of the ease with which the treatment heads can be replaced or possibly as a result of the simultaneous use of several treatment heads, the apparatus becomes extremely flexible and can be easily adapted to the specific application at hand. Because the power supply unit can be used as a base unit for all applications and only the individual treatment heads need to be replaced, considerable cost savings are obtained. The pressure pulse source, which is subject to wear, can also be replaced extremely easily and quickly simply by removing the entire treatment head and replacing it with a new one.

When different types of treatment heads are used, it is necessary in many cases for the power supply unit to be reconfigured for the selected type of treatment head. To simplify this reconfiguration and to prevent the apparatus from being used improperly, it is preferable for the supply unit to be reconfigured automatically to the treatment head connected to it at the time in question. For this purpose, the connector can contain a code, which is characteristic of the type of treatment head being used. It is also possible to integrate an electronic code into the treatment head itself, which then communicates by way of an interface in the connector with the supply unit to identify the selected treatment head for the reconfiguration of the supply unit. The supply unit or even the treatment head can contain a microprocessor with memory, or one or both can contain just memory so that, first, the operating values of the supply unit can be automatically reconfigured to suit the treatment head connected to it at the time and, possibly second, to store and display the total operating time of each individual treatment head and the number of discharges it has fired, that is, the number of pressure pulses already generated, as well as the number of discharges still possible within the ser vice life of the apparatus. As an alternative, it is also possible to utilize a memory chip in the treatment head to store the operating values (e.g., number of discharges, total operating time, etc.).

The treatment heads can be designed with different sets of characteristics, depending on their intended purpose. When reflectors are used to focus the shock waves, these semi-ellipsoids or semi-paraboloids can be provided with different ratios between the axes. When acoustic lenses are used for focussing, these can be designed with different depths of focus. In addition, spherical arrangements of electrical membranes or piezoelectric crystals with different geometric radii can be used. Using focussing devices of different designs makes it possible to realize different characteristics with respect to acoustic energy density and penetration depth.

To span various intermediate distances between the reflector aperture and the surface of the skin and to conduct the shock waves acoustically into the body, it is possible to use conduction cushions of various thicknesses instead of the conventional lead-in water gaps. The acoustic impedance of these cushions should be the same or very close to that of water and thus to that of bodily tissue.

In an advantageous embodiment, the apparatus can be equipped not only with the treatment head or set of treatment heads but also with a locating device or with a set of locating devices, one for each treatment head, to find the area to be treated. The locating device and the treatment head/heads are arranged in a defined manner with respect to each other, so that, after the area to be treated has been located, the shock waves can be focussed on this area without any additional adjustment work.

BRIEF DESCRIPTION OF THE DRAWINGS

These and other objects of the present invention and various features and details of the operation and construction thereof are hereinafter more fully set forth with reference to the accompanying drawings, wherein.

DETAILED DESCRIPTION OF THE PREFERRED EMBODIMENT

Figure 1:
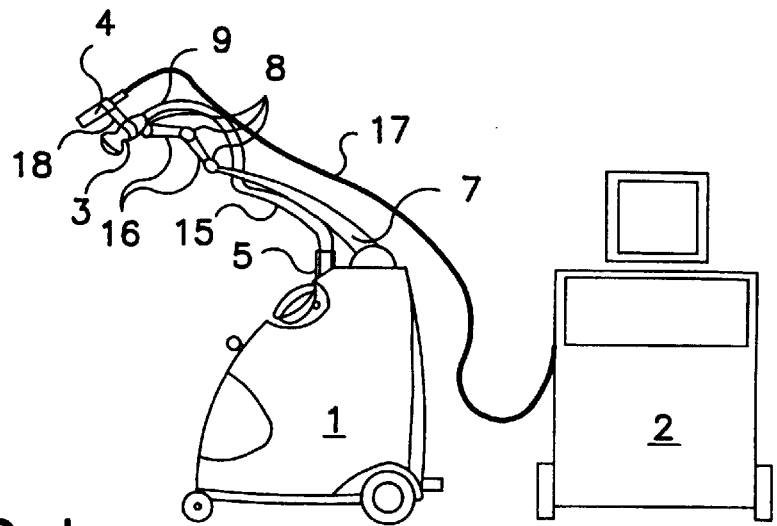
FIG. 1 is a side elevational view of an apparatus designed in accordance with the invention.

Referring now to the drawings and particularly to FIG. 1 thereof, the apparatus illustrated has a power supply unit 1 which contains all the essential electrical and electronic components. In particular, supply unit 1 has the high-voltage section with a charging unit and a discharge circuit for the electrical discharge between the electrodes of the pressure pulse source. The structure and function of these electrical supply units are known and do not constitute an object of the invention.

An arm 7 is attached to supply unit 1 in such a way that it can rotate, pivot, and be locked in position. Arm 7 can be moved into position and locked electrically, mechanically, or hydraulically. Such moving and locking are known in and of themselves and do not constitute an object of the invention.

At the free end of arm 7, at least one treatment head 3 is provided. Treatment head 3 contains a pressure pulse source 3a and a fluid medium 3 b, in which, by means of the pressure pulse source, acoustic shock waves are generated. In addition, treatment head 3 also contains a focussing device 3c, which focuses the acoustic shock waves generated by the pressure pulse source in the fluid medium on a focal point situated outside treatment head 3. Treatment head 3 is designed as a closed structural unit, which in particular also contains the fluid medium 3b in a closed volume. Treatment head 3 is detachably connected to the free end of arm 7.

Treatment head 3 is connected detachably by way of a cable 15 and a pin- and-socket connector 5 to power supply unit 1. To configure the electrical data of supply unit 1 to the electrical characteristics of treatment head 3, pin-and-socket connector 5 can be designed to contain a code, so that, when the pin-and-socket connector is connected, the correct values are necessarily made available to treatment head 3. In a different design, an electronic code stored, for example, in a memory chip, can be integrated into treatment head 3, which, when pin-and-socket connector 5 is connected, transmits the required data on the properties of treatment head 3 via an interface to supply unit 1, so that supply unit 1 can be configured automatically to the treatment head 3 attached at that particular time. Supply unit 1 contains preferably a microprocessor to configure the operating values automatically to the characteristics of connected and identified treatment head 3. Alternatively, it is also possible for supply unit 1 to transmit the operating values to a memory chip in treatment head 3 or to pin-and-socket connector 5, which stores these operating values.

Treatment head 3 is fastened in a detachable manner to the free end of arm 7. For example, it can be clamped in a suitable bracket. Because such attachments are familiar to the expert, there is no need to describe them in detail here.

To achieve a simple and exact positioning of treatment head 3, articulated arms 16 are attached to the free end of arm 7, these articulated arms being connected to arm 7 and each other by lockable joints 8. For the exact positioning of treatment head 3, arm 7 is first moved roughly into position and locked. Then joints 8 of articulated arms 16 are loosened, and the position of treatment head 3 is finely adjusted by moving articulated arms 16. Joints 8 can be locked either electrically, mechanically, or hydraulically.

In a preferred design, a locating device 4 is attached to the free end of arm 7 in addition to treatment head or heads 3. Locating device 4 is preferably designed as an ultrasonic head, e.g., a "linear array ultrasonic scanner", which is connected by a cable 17 to an ultrasound unit 2. Ultrasound unit 2 contains the power supply for ultrasound head 4 and a monitor, etc. Ultrasound devices of this type are known in and of themselves.

So that the focus of treatment head 3 can be positioned easily, quickly, and exactly on treatment site 6 in the body oft he patient, treatment head or heads 3 and locating device 4 are preferably attached to a support bracket 18, which is arranged attached to the free end of arm 7 or of articulated arms 16. Support bracket 18 establishes an exact correlation between the positions of locating device 4 and treatment head or heads 3. This positional correlation makes it possible for the focus of treatment head or heads 3 to be positioned exactly on treatment site 6 as soon as treatment site 6 has been located by locating device 4.

Figure 2:
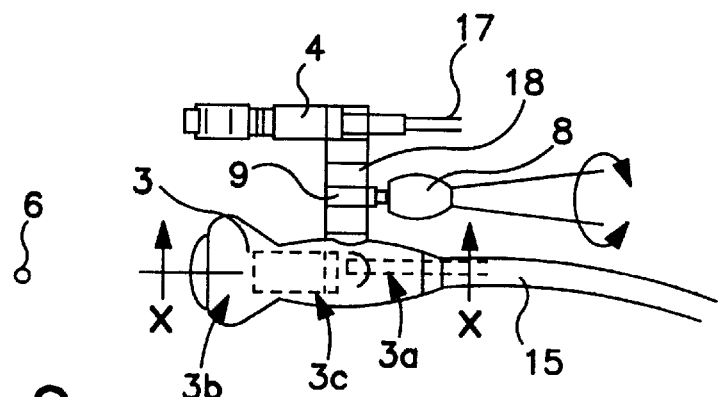
FIG. 2 shows the arrangement of a treatment head and a locating device.

In the exemplary embodiment according to FIG. 2, support bracket 18 is attached to joint 8 at the free end of jointed arms 16 by means of a rotary joint 9, so that the bracket is free to turn. Treatment head 3 can be attached to one end of support bracket 18 and the locating device 4 to the other end.

To position the head, arm 7 is first roughly aligned. Then, after joints 8 have been loosened, articulated arms 16 are used to adjust locating device 4 in such a way that it is aimed at treatment site 6 as a target point. With the device in this position, joints 8 are now locked. Support bracket 18 is then pivoted around rotary joint 9, as a result of which the locating device 4 and treatment head 3 swap positions; treatment head 3 is thus brought automatically into a position where it is focussed on treatment site 6.

It is obvious without further explanation that, instead of a pivoting motion of support bracket 18 around rotary joint 9, it is also possible for support bracket 18 to execute a sliding motion or to perform a combination of rotational and sliding movements in order to realize the exchange of positions between locating device 4 and treatment head 3.

Figure 3:
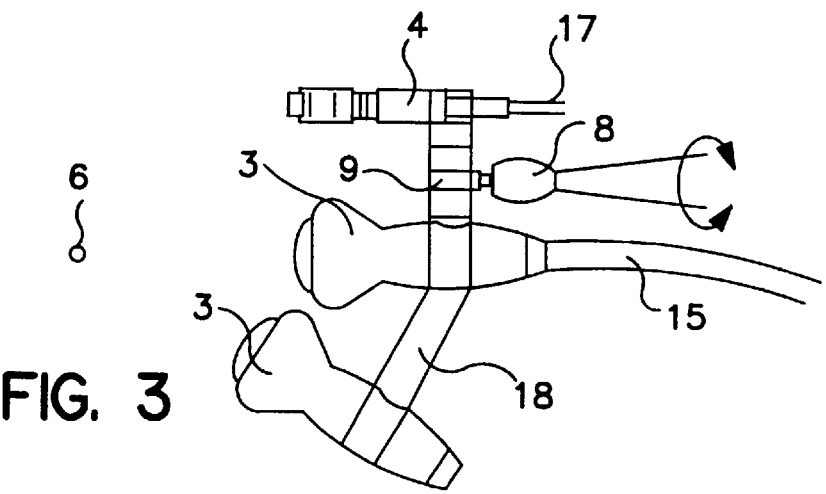
FIG. 3 shows the arrangement of two treatment heads and one locating device.

FIG. 3 shows a design in which two treatment heads 3 can be attached to support bracket 18, both being connected by way of pin-and-socket connectors 5 to power supply unit 1. The two treatment heads 3 are arranged on support bracket 18 in such a way that their respective foci coincide. In this design, arm 7 and articulated arms 16 are again used first to locate treatment site 6 of the patient by means of locating device 4, whereupon arm 7 and articulated arms 16 are locked in the corresponding position. Then support bracket 18 is rotated around rotary joint 9, so that the common focus of the two treatment head 3 are shifted to treatment site 6 as identified by locating device 4.

When the geometry of the area of the patient to be treated allows for such an arrangement, a design of this type with two treatment heads 3 can be used to shorten the treatment time as a result of the higher acoustic energy input provided by two treatment heads 3. With this design, more energy can be supplied to treatment site 6 in the same period of time. It is also possible in this design to use two treatment heads 3 with different characteristics. As a result, pressure pulses with the same or different properties can be superimposed simultaneously or in sequence in order to optimize or minimize biological or acoustomechanical effects in the body.

Figure 4:
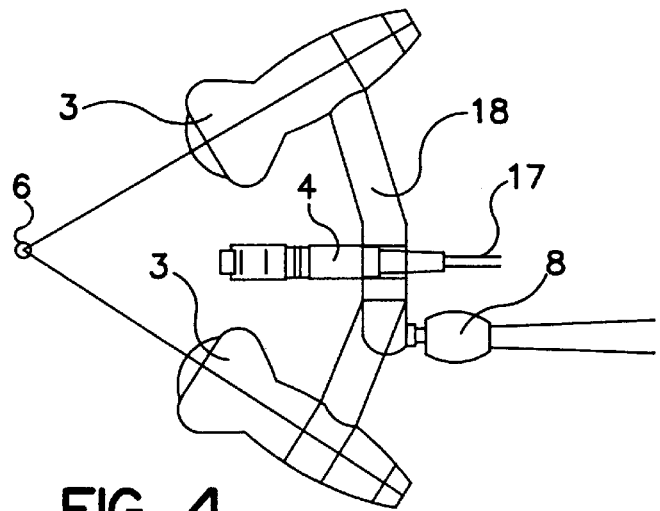
FIG. 4 shows a different design of an arrangement of two treatment heads and one locating device.

FIG. 4 shows a variant in which, again, two treatment heads 3 with the same or different characteristics are used. In this design, the two treatment heads 3 are arranged at the ends of support bracket 18, whereas locating device 4 is located in the central area of support bracket 18. Treatment heads 3 and positioning device 4 can be attached to support bracket 18 in such a way that the foci of treatment heads 3 fall on the target point of locating device 4. Once locating device 4 is aligned with treatment site 6, the foci of treatment heads 3 are automatically located on this treatment site 6 also.

This design has the advantage over the design according to FIG. 3 that no additional revolving motion of support bracket 18 is required. Nevertheless, the angle between the direction in which the waves are emitted by treatment heads 3 and the target direction of locating device 4 is larger than in the previous design, which under certain conditions can cause the shock waves to cast shadows.

The two treatment heads 3 and locating device 4 do not have to be on the same plane as illustrated in FIG. 4. Treatment heads 3 and locating device 4 can also be at an angle to each other. It is also possible to install more than two treatment heads 3, which surround locating device 4 in the form of a ring or some other pattern.

Figure 5:
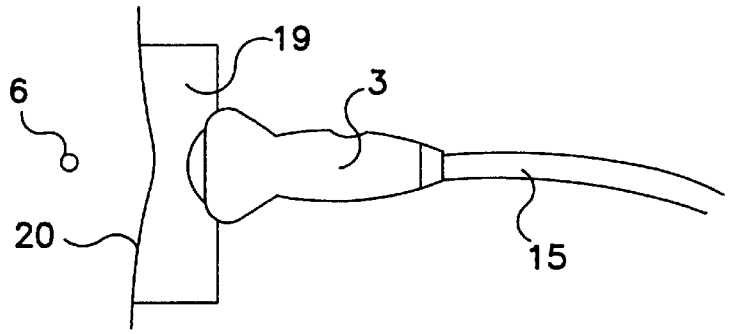
FIG. 5 shows two treatment heads with different penetration depths.

FIG. 5 shows two different designs of treatment head 3, which differ with respect to their focal or penetration depth in order that treatment sites 6 situated at different depths below the surface of the body can be treated. A conduction cushion 19 can be placed between surface 20 of the body and the end of treatment head 3 to span the various distances. Conduction cushions 19 are designed as pressure-tight, closed fluid volumes or as elastically deformable solids. Conduction cushions 19 have an acoustic impedance which is as close as possible to that of body tissue. For this purpose, conduction cushions 19 are filled with water or consist of a suitable plastic, e.g., polyurethane. By replacing the treatment heads and reconnecting pin-and-socket connectors 5, the apparatus can be adjusted to the treatment depth required in the individual case.

Figure 6:
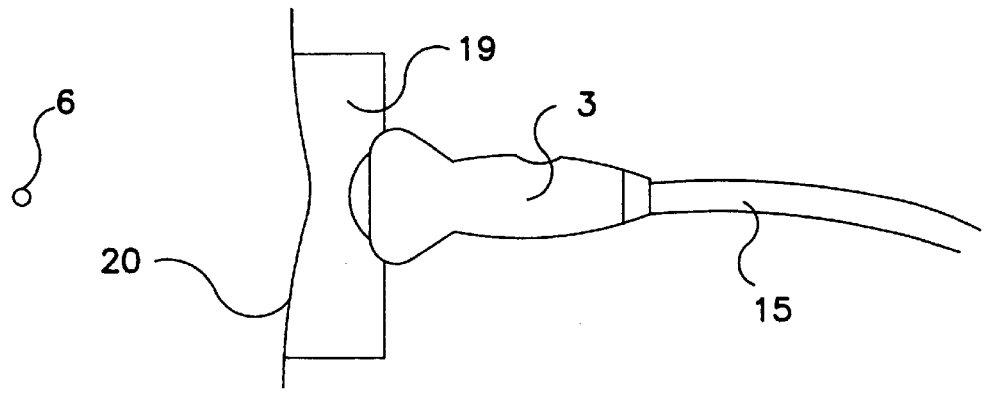
FIG. 6 shows a design of the treatment head according to the invention in an axial cross section.
Figure 6:
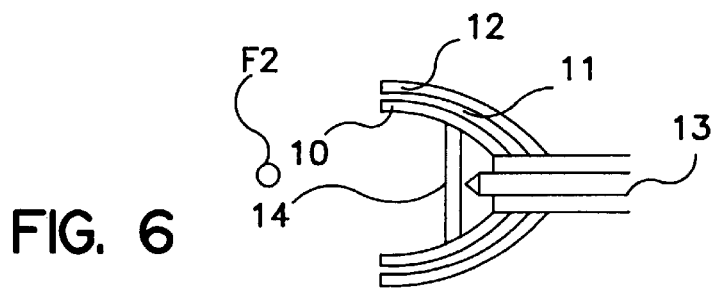

FIG. 6 shows an exemplary embodiment of a treatment head 3 such as that used preferably in the apparatus according to the invention.

Treatment head 3 has two electrodes 13, 14, which form a spark gap in a fluid medium, which is enclosed by a reflector 10 and an exciting membrane (not shown). The spark gap formed by electrodes 13, 14 is located at one of the foci of reflector 10, which has either an elliptical, a parabolic, or a spherical design.

Reflector 10 is preferably produced out of sheet metal by a shaping process such as spinning. As a result, a significant cost reduction is achieved in comparison with conventional reflectors, which are turned, cast, injected, or milled. The cost reduction is based essentially on the more favorable production process, on the decrease in the amount of material required, and on the lower cost of the starting material. In addition, the weight of treatment head 3 is also reduced. The lower production costs and reduced weight have especially advantageous effects when, according to the invention, a large number of different treatment heads 3 are available for exchange or when worn-out treatment heads 3 must be replaced.

The thickness oft he wall of reflector 10 should be no more than 5 mm throughout, that is, in all areas of reflector 10. A wall thickness of ≦3 mm is preferred. Nevertheless, the wall thickness may not fall below a minimum value of about 1 mm, because otherwise pressure waves in certain frequency ranges are not sufficiently reflected, so that the shock wave pulse does not have the desired form.

Thin-walled reflector 10 can be enclosed by an outside shell 12 of plastic, an air layer 11 thus being formed between reflector 10 and outside shell 12. Air layer 11, in conjunction with outside shell 12 of plastic, improves the reflective properties of the reflector and also forms a sound-insulating jacket around treatment head 3.

Figure 7A:
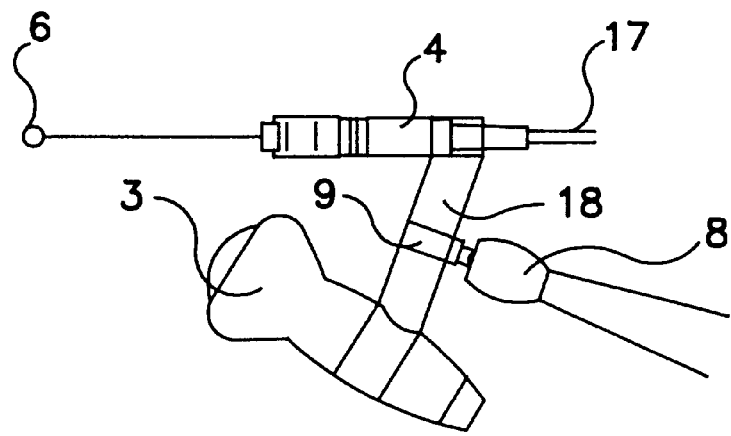
FIGS. 7a and 7b show another design with a treatment head and a locating device.
Figure 7B:
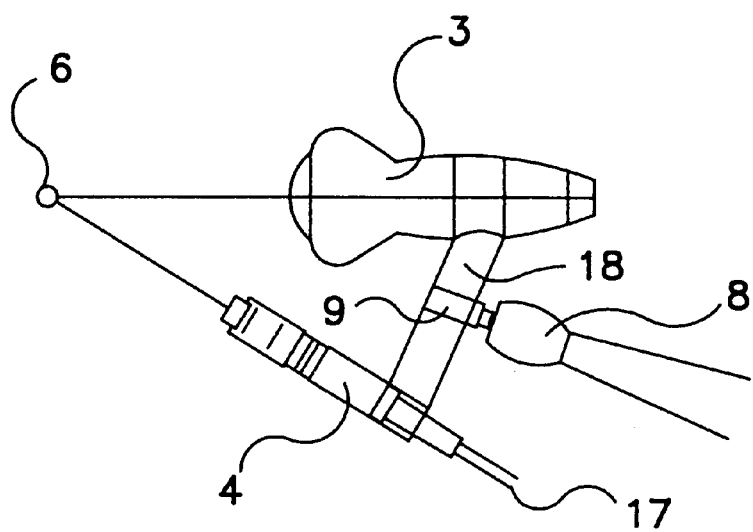

FIGS. 7a and 7b show a design which, like the design of FIG. 2, comprises a treatment head 3 and a locating device 4. Treatment head 3 and locating device 4 are arranged on support bracket 18, which pivots around rotary joint 9, in such a way that locating device 4 is aimed at the focus of treatment head 3. When treatment site 6 is brought into the proper position in the ultrasound image of locating device 4, as shown in FIG. 7a, then, by means of rotary joint 9, the position of treatment head and locating device 4 are exchanged, as shown in FIG. 7b. In this design, the routes traveled by the sound waves of the ultrasound locating device 4 and by those of treatment head 3 are nearly identical, so that the effects of diffraction and scattering are the same for both the locating device and the treatment head.

It is also advantageous in this design that locating device 4 remains aimed at treatment site 6 during the treatment by treatment head 3, as shown in FIG. 7. It is thus possible to keep treatment site 6 under observation on-line during the treatment by means of the locating device.

Even though particular embodiments of the invention have been illustrated and described herein, it is not intended to limit the invention and changes and modifications may be made therein within the scope of the following claims.

What is claimed is:

1. Apparatus for administering acoustic shockwaves into a body, comprsing:
   at least one detachble treatment head with electrical cable and detachable connector for applying acoustic shockwaves to an area in a body to be therapeutically treated;
   a power supply unit with means for supporting and accurately positioning treatment heads;
   code means for storing electrical signals including electrical parameters embedded in said treatment head to store data and transmit treatment head characteristics to said power supply unit;
   means within the power supply unit to identify the treatment head characteristics connected to it; and
   means within the power supply unit to interpret coded signals and automatically reconfigure electrical output to match treatment heads characteristics.

2. Apparatus according to claim 1, characterized in that the treatment heads have different focussing properties or acoustic penetration depths.

3. Apparatus according to claim 2, characterized in that the different penetration depths are accomplished by the use of by different conduction elements.

4. Apparatus according to claim 3, characterized in that the conduction element comprises a closed water cushion.

5. Apparatus according to claim 3, characterized in that the conduction element comprises or a plastic body of, for example, polyurethane.

6. Apparatus according to claim 2, characterized in that the different focussing properties are achieved by different geometries of the reflector (10), by different acoustic lenses, or by different radii of curvature in a spherical design of the pressure pulse source.

7. Apparatus according to claim 1, including at least two treatment heads, which can be operated separately or simultaneously.

8. Apparatus according to claim 1, including device arranged in a predetermined positional relationship with treatment head.

9. Apparatus according to claim 8, wherein said locating device is an ultrasound sensor, preferably a linear array ultrasonic scanner.

10. Apparatus according to claim 8, wherein the focus of the treatment head, coincides with the target area of the locating device.

11. Apparatus according to claim 8, wherein the locating device and the treatment head are mounted in a position-exchanging manner in such a way that, as a result of the exchange of positions, the focus of the treatment head, arrives at the target area of the locating device.

12. Apparatus according to claim 11, wherein the locating device and the treatment head are attached to a support bracket (18), which can be rotated and or otherwise displaced for the exchange of positions.

13. Apparatus according to claim 1, wherein connection of the treatment head to the power supply unit comprises at least one pin-and-socket connector.

14. Apparatus according to claim 1, wherein the electrical operating values of the supply unit are automatically configured to suit the identified treatment head.

15. Apparatus according to claim 1, wherein the supply unit stores and displays the number of shock wave pulses, the operating time, etc., of the individual treatment heads.

16. Apparatus according to claim 1, wherein the treatment head stores the number of shock wave pulses, the operating time, etc., these values being read as needed and processed as well as displayed via the supply unit.

17. Apparatus according to claim 1, wherein at least two treatment heads are connected, which emit the same or different pressure pulses simultaneously or in sequence.

18. Apparatus according to claim 1, wherein the treatment head has a metal reflector with a wall thickness of $\leq 5$ mm, and preferably of 1–3 mm.

19. Apparatus according to claim 18, wherein the reflector is made of sheet metal by a shaping process, especially by metal spinning.

20. Apparatus according to claim 19, wherein the reflector is surrounded by an air layer and an external shell in a sandwich design.

21. Apparatus for administering acoustic shockwaves into a body, comprising:
   detachable treatment heads with electrical cable and pin-and-socket connector for applying said shockwaves to an area in said body to be therapeutically treated,
   a power supply unit with means for supporting and accurately positioning treatment heads;
   code means for storing electrical signals including electrical parameter in said treatment head to store data and transmit treatment head characteristics via said pin-and-socket connector to said power supply unit;
   mean within the power supply unit to identify the treatment head characteristics connected to it; and
   means within the power supply unit to interpret coded signals and automatically reconfigure electrical parameters to match treatment head characteristics.

22. Apparatus for administering acoustic shockwaves into a body, comprising:
   detachable treatment heads with electrical cable and pin-and-socket connector for applying said shockwaves to an area in said body to be therapeutically treated;
   a power supply unit with means for supporting and accurately positioning treatment heads;
   code means for storing electrical signals including electrical parameters embedded in said treatment heads to store data and transmit treatment head characteristics to said power supply unit;
   means within the power supply unit to identify the treatment head characteristics connected to it; and
   means within the power supply unit to interpret coded signals and automatically reconfigure electrical output to match treatment heads characteristics.

23. An apparatus for administering acoustic shockwaves into a body, comprising;
   at least one treatment head for applying acoustic shockwaves to an area in a body to be therapeutically treated;
   a power supply unit with means for supporting and accurately positioning treatment heads;
   code means for storing electrical signals including electrical parameters in connector means of said treatment head to store data and transmit treatment head characteristics to said power supply unit;
   means within said power supply unit to identify the treatment head characteristics connected to it; and
   means within said power supply unit to interpret coded signals and automatically reconfigure electrical parameters to match treatment head characteristics.

* * * * *